United States Patent [19]
Wehinger et al.

[11] Patent Number: 4,483,985
[45] Date of Patent: Nov. 20, 1984

[54] PRODUCTION OF 1,4-DIHYDROPYRIDINECARBOXYLIC ACIDS

[75] Inventors: Egbert Wehinger, Velbert; Friedrich Bossert, Wuppertal, both of Fed. Rep. of Germany

[73] Assignee: Bayer Aktiengesellschaft, Leverkusen, Fed. Rep. of Germany

[21] Appl. No.: 226,286

[22] Filed: Jan. 19, 1981

Related U.S. Application Data

[62] Division of Ser. No. 84,338, Oct. 12, 1979, Pat. No. 4,285,955.

[51] Int. Cl.$^3$ .................. C07D 279/10; C07D 213/22; C07D 217/02; C07D 211/68
[52] U.S. Cl. .................... 544/131; 546/321; 546/257; 546/258; 546/167; 546/144; 546/281; 546/193; 546/194; 544/238; 544/333; 544/405; 544/284; 544/353; 544/365; 260/244.4
[58] Field of Search .............. 546/321, 257, 258, 167, 546/144, 281, 193, 194; 544/238, 333, 405, 284, 353, 131

[56] References Cited

PUBLICATIONS

Noller, Textbook of Organic Chemistry, 2nd Edition, W. B. Saunders Company, Philadelphia, 1958.

Primary Examiner—Alan L. Rotman
Assistant Examiner—Robert C. Whittenbaugh
Attorney, Agent, or Firm—Sprung, Horn, Kramer & Woods

[57] ABSTRACT

The invention relates to a process for the production of 1,4-dihydropyridinecarboxylic acid compounds which involves hydrolysis, under alkaline conditions and in a temperature range from 10° to 100° C., of an ester group which contains an electron-attracting group. The invention also includes novel compounds made according to the invention as well as compositions containing said novel compounds. Also included in the invention are methods for the use of said compounds and compositions. The compounds obtained according to the process of the invention are useful because of their circulation-influencing action and are also useful as intermediates for the preparation of compounds having circulation-influencing action.

10 Claims, No Drawings

PRODUCTION OF 1,4-DIHYDROPYRIDINECARBOXYLIC ACIDS

This is a division of application Ser. No. 084,338, filed Oct. 12, 1979 now U.S. Pat. No. 4,285,955 issued Aug. 25, 1981.

The present invention relates to an unobvious process for the production of certain 1,4-dihydropyridinecarboxylic acid compounds, some of which are known, to the pharmaceutical use of the products and to their use as intermediate products in the production of agents which influence the circulation.

It has already been disclosed that N-aryl-substituted dihydropyridine-3,5-dicarboxylic acid esters can be converted, under the action of alkalis, into corresponding dihydropyridinemonocarboxylic acids and dihydropyridine-dicarboxylic acids (compare Br. Lachowicz, Monatsh. Chem. 17, 343 (1896)).

Further, it has been disclosed that N-alkyl-substituted dihydropyridinemonocarboxylic acids are obtainable from the corresponding 3,5-diesters in a similar manner, by alkaline hydrolysic (compare A. E. Sausin et al., Gieterosiklich Scedin 1978, (2) 272).

In contrast to the easy saponificability of N-aryl- and N-alkyl-substituted dihydropyridine-3,5-dicarboxylic acid diesters, N-unsubstituted dihydropyridinedicarboxylic and diesters can either not be hydrolysed at all or only be hydrolysed in very poor yields to the corresponding monocarboxylic acids and dicarboxylic acids (compare U. Eisner et al., Chem. Rev. 72, 1, 41 (1972); B. Loev et al., J. heterocyclic Chem. 12, 363 (1975)).

According to the present invention there is provided a process for the production of a compound which is an N-unsubstituted 1,4-dihydropyridine-carboxylic acid of the general formula

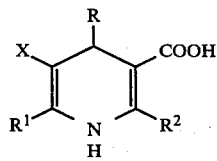

(I)

or its salt,
in which
R denotes an aryl radical or a heterocyclic radical, selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl and quinoxalyl, in which the aryl radical or the heterocyclic radical optionally contains 1 or 2 or 3 identical or different substituents selected from phenyl, alkyl, alkenyl, alkinyl, alkoxy, alkylene, dioxyalkylene, halogen, trifluoromethyl, trifluoromethoxy, alkylamino, nitro, cyano, azido, carboxamido, sulphonamido and $SO_m$—alkyl (in which m is 0, 1 or 2), $R^1$ and $R^2$ are identical or different and denote a hydrogen atom, a straight-chain or branched alkyl radical, an aryl radical or an aralkyl radical and X (a) denotes a —COOH group or
 (b) denotes a group of the formula —$COR^3$,
in which $R^3$ denotes an optionally substituted alkyl, aryl, aralkyl, amino, monoalkylamino or dialkylamino group or (c) denotes a group of the formula —$COOR^4$,
in which $R^4$ denotes a straight-chain, branched or cyclic, saturated or unsaturated hydrocarbon radical which is optionally interrupted by an oxygen or a sulphur atom (to form an oxa- or aza-hydrocarbon radical) or by an —SO— or —$SO_2$—group in the chain, and/or which is optionally substituted by one halogen or by 1 or 2 trifluoromethyl groups or by one phenyl, phenoxy, phenylthio or phenylsulphonyl group, which in turn is optionally substituted by halogen, cyano, dialkylamino, alkoxy, alkyl, trifluoromethyl or nitro, or in which the hydrocarbon radical is optionally substituted by pyridyl or amino, these amino groups carrying two identical or different substituents selected from alkyl, alkoxyalkyl, aryl and aralkyl, and these substituents optionally form, with the nitrogen atom, a 5- to 7-membered ring which optionally contains an oxygen or sulphur atom or the N-alkyl grouping as a further hetero-atom, or (d) denotes a group of the formula —$S(O)_r$—$R^5$
in which
r is 0, 1 or 2 and
$R^5$ denotes a straight-chain, branched or cyclic, saturated or unsaturated aliphatic hydrocarbon radical, optionally interrupted by an oxygen atom in the chain and/or which is optionally substituted by amino or an aryl radical selected from phenyl, phenoxy, phenylthio and phenylsulphonyl, and pyridyl, the aryl radical being optionally substituted by halogen, cyano, dialkylamino, alkoxy, alkyl, trifluoromethyl or nitro, and the amino group being optionally substituted by 2 identical or different substituents selected from alkyl, alkoxyalkyl, aryl and aralkyl, these substituents optionally form, with the nitrogen atom, a 5- to 7-membered ring which optionally contains an oxygen or sulphur atom or the N-alkyl grouping as a further hetero-atom, or in which $R^5$ denotes an aryl radical which optionally contains 1 to 3 identical or different substituents selected from alkyl, alkoxy, halogen, cyano, trifluoromethyl, trifluoromethoxy, dialkylamino and nitro, in which a 1,4-dihydropyridine derivative of the formula

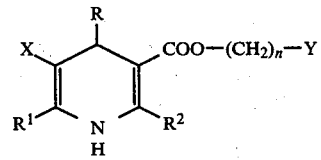

(II)

in which
R, $R^1$, $R^2$ and X have the above-mentioned meanings,
n is 1, 2, 3 or 4, and
Y denotes an electron-attracting group is hydrolysed under alkaline conditions in the presence of an inert organic solvent in a temperature range from 10° to 100° C.

As used herein and unless otherwise indicated, the terms "alkyl", "alkenyl", "alkinyl", "alkoxy", "alkylene", "dioxyalkylene", "alkylamino", "dialkylamino", and "alkoxyalkyl" refer to moieties in which each hydrocarbon portion contains preferably up to 8 carbon atoms; the term "aryl" refers to preferably mono- or bi-cyclic carbocyclic aryl, such as phenyl, biphenyl and naphthyl; the term "halogen" refers preferably to chlorine, bromine and fluorine; the term "aralkyl" refers preferably to moieties in which the aryl portion is as defined above for "aryl" and the alkyl portion contains 1 to 2 carbon atoms; the term "saturated or unsaturated hydrocarbon radical" refers preferably to alkyl, oxaalkyl, thia-alkyl, alkenyl, oxa-alkenyl, thia-alkenyl, alkinyl, oxa-alkinyl, thia-alkinyl each of which contains up to 8 carbon atoms; cycloalkyl, cycloalkenyl, cycloalkadienyl, cyclo-oxa-alkyl, cyclo-thia-alkyl, cyclo-axa-alkenyl, cyclo-thia-alkenyl, each containing 4 to 7, preferably 5 to 6 ring members, as well as the S-oxides and dioxides of each of said moieties.

A resulting basic compound can be converted into a corresponding acid addition salt (especially a therapeutically useful acid-addition salt), for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluenesulfonic, naphthalenesulfonic and sulfanilic acid; methionine, tryptophan, lysine and arginine.

It is distinctly surprising that using the process according to the invention the 1,4-dihydropyridinecarboxylic acids of formula (I) are obtained in such good yields and high purity, since it had to be expected, in view of the prior art, that the N-unsubstituted 1,4-dihydropyridinecarboxylic acids would, under these hydrolysis conditions, either not be obtainable at all or only be obtainable in very poor yields (compare B. Loev et al., J. Heterocyclic Chem. 12, 363 (1975)). The process of the present invention accordingly overcomes an existing prejudice against the hydrolysability of N-unsubstituted dihydropyridinecarboxylic acid esters.

An important advantage of the process, in addition to the good yields and high purity of the product obtained, is that because of its simple reaction conditions it can be carried out with little technical effort and with great economy.

DT-OS (German Published Specification) No. 2,218,644 already mentions some dihydropyridinemonocarboxylic acids as starting materials for an ester synthesis, and also mentions that they can in principle be prepared by alkaline hydrolysis of corresponding diesters. However, most of the dihydropyridine monocarboxylic acids mentioned there are substituted at the nitrogen in the 1-position. Moreover, physico-chemical parameters and data on yields, or concrete process measures for carrying out the hydrolysis, are not disclosed there.

As already explained in the comments on the prior art, it has hitherto only been possible to saponify the dihydropyridinedicarboxylic acid diesters without problems when they possess a substituent at the nitrogen in the 1-position. The saponification of N-unsaturated dihydropyridines hitherto either did not succeed at all or only succeeded with such low yields that carrying out the process industrially appeared uninteresting.

Surprisingly, the introduction of an electron-attracting group into the ester radical to be split off permits simple saponification to give the N-unsubstituted monocarboxylic acids of formula (I) which were hitherto difficult to obtain.

Particularly preferred ester groups which can be split off are alkyl groups with 1 to 4 carbon atoms, which are substituted by electron-attracting groups, preferably by cyano, acetoxy, alkoxy with 1 to 4 carbon atoms, dioxolane, fluorine or chlorine. The cyanoethyl radical should be singled out as a particularly preferred radical.

The dihydropyridinecarboxylic acids of formula (I), prepared according to the invention, themselves possess valuable pharmacological properties. Because of their circulation-influencing action they can be used, for example, as anti-hypertensive agents, as peripheral and cerebral vasodilators and as coronary therapeutics.

In addition, they are particularly suitable for use as starting materials for the preparation of dihydropyridinecarboxylic acid diesters which in turn exhibit valuable pharmacological properties, especially a circulation-influencing action (see U.S. Pat. No. 3,799,934). The preparation of these diesters is usually carried out in accordance with known methods of esterification, for example by reaction in accordance with the dicyclohexyl-carbodiimide method (DCC method) (compare Angew. Chem. 90, 556 et seq. (1978)) or by reaction of the corresponding dihydropyridinecarboxylic acid imidazolides with alcohols (compare H. A. Staab et al. Neuere Methoden der Präparativen Organ. Chemie. (Recent Methods of preparative Organic Chemistry), Volume V, page 53 et seq. (1967)).

The 1,4-dihydropyridinecarboxylic acids prepared according to the invention, especially the examples of this compound category which were not previously known, are valuable starting materials from which (a) dihydropyridine-3,5-dicarboxylic acid esters with nonidentical ester groups can be prepared in high purity under mild conditions, by introducing the second alcohol ester component specifically into the molecule, and (b) labelled dihydropyridine diesters can be prepared in a simple manner by introducing a deuterium-labelled or tritium-labelled alcohol radical, such as, for example, a pertritiated methylate radical, and hence the preparation of these labelled compounds may be carried out in one step.

Such diesters are of particular importance for investigations of the metabolism of medicinal active compounds.

If 1,4-dihydro-2,6-dimethyl-4-(3'-nitrophenyl)-pyridine-3,5-dicarboxylic acid 2-cyanoethyl isopropyl ester is used as the starting material, the course of the reaction can be represented by the following equation:

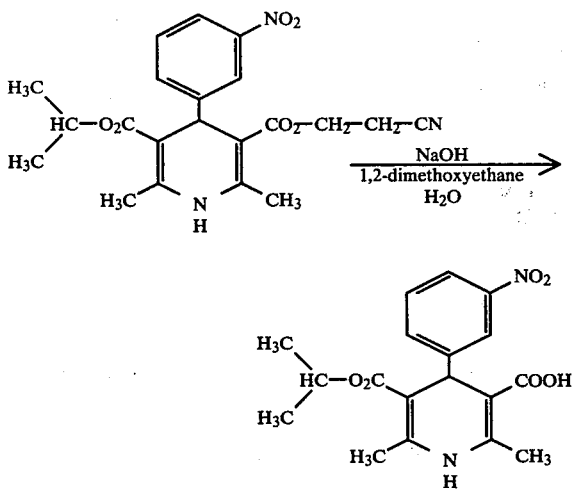

Using the process according to the invention, a 1,4-dihydropyridine derivative of formula (II) is preferably hydrolysed in the presence of an alkali metal hydroxide, especially in the presence of a water-miscible organic solvent, and preferably in a temperature range from 20° to 50° C.

In the formula (II), R preferably denotes a phenyl or naphthyl radical or heterocyclic radical selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical. The heterocyclic radicals mentioned, and in particular the phenyl radical, contain 1 or 2 identical or different substituents, said substituents being preferably phenyl, straight-chain or branched alkyl with 1 to 8, especially 1 to 4, carbon atoms, cycloalkyl with 3 to 7 carbon atoms, alkenyl or alkinyl with 2 to 6 carbon atoms, especially 2 to 3 carbon atoms, alkoxy with preferably 1 to 4, especially 1 or 2, carbon atoms, trimethylene, tetramethylene and pentamethylene, dioxymethylene, halogen, such as fluorine, chlorine, bromine and iodine, especially fluorine, chlorine, or bromine, trifluoromethyl, trifluoromethoxy, nitro, cyano, azido, monoalkylamino and dialkylamino with preferably 1 to 4, especially 1 or 2, carbon atoms per alkyl group, carboxamido, sulphonamido or $SO_m$—alkyl, wherein m is 0, 1 or 2 and alkyl preferably contains 1 to 4, especially 1 or 2, carbon atoms.

Furthermore, in formula (II), $R^1$ and $R^2$, which may be identical or different, preferably denote a hydrogen atom, a straight-chain or branched alkyl radical with 1 to 4, especially 1 to 3, carbon atoms, a phenyl radical or an aralkyl radical, especially a benzyl radical, n preferably is 1, 2, 3 or 4, especially 2, X preferably denotes a carboxyl group —COOH or preferably denotes the group —CO—$R^3$, in which $R^3$ preferably denotes a straight-chain or branched alkyl radical with 1 to 4 carbon atoms, a phenyl radical, a benzyl radical or an amino, monoalkylamino or dialkylamino group with up to 4 carbon atoms per alkyl group, the alkyl groups of the dialkylamino group optionally forming, with the nitrogen atom, a 5-membered to 7-membered ring which can contain an oxygen or sulphur atom as a further hetero-atom, or X preferably denotes the group —COOR$^4$, wherein $R^4$ preferably denotes a straight-chain, branched or cyclic, saturated or unsaturated hydrocarbon radical with up to 8, especially with up to 6, carbon atoms, which is optionally interrupted in the chain by an oxygen atom or a sulphur atom or the —SO— or —SO$_2$—group, and/or in which a hydrogen atom can be replaced by a halogen atom, such as fluorine or chlorine, or by one or two trifluoromethyl groups, or by a phenyl, phenoxy, phenylthio or phenylsulphonyl group (which four last-mentioned groups are optionally substituted by halogen, especially fluorine, chlorine or bromine, cyano, dialkylamino with 1 or 2 carbon atoms per each alkyl group, alkoxy with 1 to 4 carbon atoms, alkyl with 1 to 4 carbon atoms, trifluoromethyl or nitro) or by an α-, β- or γ-pyridyl group or by an amino group, which amino group carries two identical or different substituents from the group of alkyl with up to 4 carbon atoms, alkoxyalkyl with up 4 carbon atoms, phenyl and aralkyl, especially benzyl, which substituents optionally form, with the nitrogen atom, a 5- to 7-membered ring which can contain, as a further hetero-atom, an oxygen or sulphur atom or the N-alkyl groupings, the alkyl group preferably containing 1 to 3 carbon atoms, or X preferably denotes the group —S-(O)$_r$—R$^5$, in which r is 0, 1 or 2 and R$^5$ preferably denotes a straight-chain, branched or cyclic, saturated or unsaturated aliphatic hydrocarbon radical with up to 8, especially up to 6, carbon atoms, which is optionally interrupted by 1 oxygen atom in the chain and/or in which a hydrogen atom can be replaced by a phenyl, phenoxy, phenylthio or phenylsulphonyl group (which four last-mentioned groups are optionally substituted by halogen, especially fluorine, chlorine or bromine, cyano, dialkylamino with 1 or 2 carbon atoms per each alkyl group, alkoxy with 1 to 4 carbon atoms, alkyl with 1 to 4 carbon atoms, trifluoromethyl or nitro) or by an α-, β- or γ-pyridyl group or by an amino group, which amino group carries two identical or different substituents from the group of alkyl with up to 4 carbon atoms, alkoxyalkyl with up to 6, especially with up to 4, carbon atoms, phenyl and aralkyl, especially benzyl, which substituents optionally form, with the nitrogen atom, a 5- to 7-membered ring which can contain, as a further heteroatom, an oxygen or sulphur atom or the N-alkyl grouping, the alkyl group preferably comprising 1 to 3 carbon atoms, or in which $R^5$ denotes an aryl radical, especially a phenyl radical, which can optionally carry 1, 2 or 3 identical or different substituents, and where substituents contemplated are straight-chain or branched alkyl with 1 to 4 carbon atoms, alkoxy with 1 or 2 carbon atoms, halogen, especially fluorine, chlorine or bromine, cyano, trifluoromethyl, trifluoromethoxy, dialkylamino with 1 or 2 carbon atoms per each alkyl group or nitro, and Y denotes an electron-attracting group, preferably a fluorine or chlorine atom, or preferably represents the azido or nitro group or preferably denotes the ester group of the formula —COOR$^6$, in which R$^6$ represents an alkyl radical with up to 4 carbon atoms, especially with up to 2 carbon atoms, or an aralkyl radical, especially the benzyl radical, or Y preferably denotes the $$-O-\overset{O}{\underset{\|}{C}}-R^7 \text{ group,}$$

in which $R^7$ denotes an alkyl radical with up to 4 carbon atoms, especially with up to 2 carbon atoms, or a phenyl radical which is optionally substituted by chlorine, cyano or nitro, or Y preferably denotes a cyano group.

Particular interest attaches to the preparation according to the present invention of a compound of the general formula (I) or its salt,
in which
  R denotes a pyridyl radical or a phenyl radical which contains one or two identical or different substituents selected from halogen, nitro, cyano, trifluoromethyl, azido, trifluoromethoxy or alkoxy with 1 or 2 carbon atoms,
  $R^1$ and $R^2$ are identical or different and denote a hydrogen atom, an alkyl group with 1 or 2 carbon atoms, a phenyl radical or a benzyl radical and
  X (a) denotes the group —COOH
or
  (b) denotes the group —$COR^3$,
in which
  $R^3$ denotes an alkyl group with 1 to 4 carbon atoms,
or
  (c) denotes the group —$COOR^4$,
in which
  $R^4$ denotes a straight-chain, branched or cyclic, saturated or unsaturated hydrocarbon radical, which is optionally interrupted in the chain by an oxygen or sulphur atom or by the —$SO_2$—group, or denotes a benzyl radical,
or
  (d) denotes the group —$SO_2$—$R^5$,
in which
  $R^5$ denotes a straight-chain or branched, saturated or unsaturated hydrocarbon radical with up to 6 carbon atoms, or a phenyl radical, As starting compound, it is preferred to employ those dihydropyridines of the general formula (II)
in which
  R, $R^1$, $R^2$ and X have the above-mentioned meanings,
  n is 2 and
  Y denotes a fluorine or chlorine atom, a cyano group or an ester group of the formula —$COOR^6$,
  $R^6$ denoting an alkyl group with 1 or 2 carbon atoms or a benzyl radical, or denotes group —O—CO—$R^7$,
  $R^7$ denoting an alkyl group with 1 or 2 carbon atoms or phenyl.

Particular interest attaches to the use of those dihydropyridines of the general formula (II), in which
  n is 2 and
  Y denotes a cyano group, a chlorine atom or an acetoxy group.

The 1,4-dihydropyridine derivatives of the general formula (II) used as starting materials are known or can be obtained in a manner which is in itself known by reaction of ylidenecarbonyl compounds with enaminocarboxylic acid esters or by reaction of aldehydes with enamino compounds and β-ketocarboxylic acid esters (compare DT-OS (German Published Specification) 2,117,571, British Pat. No. 1,358,951, DT-OS (German Published Specification) No. 2,117,572 and British Pat. No. 1,331,405).

The following may be mentioned as examples: 1,4-dihydro-2,6-dimethyl-4-(2'nitrophenyl)-pyridine-3,5-dicarboxylic acid methyl 2-cyanoethyl ester; 1,4-dihydro-2,6-dimethyl-4-(3'nitrophenyl)-pyridine-3,5-dicarboxylic acid butyl 2-cyanoethyl ester; 1,4-dihydro-2,6-dimethyl-4-(3'-nitrophenyl)-pyridine-3,5-dicarboxylic acid isopropyl 2-cyanoethyl ester; 1,4-dihydro-2,6-dimethyl-4-(3'-nitrophenyl)-pyridine-3,5-dicarboxylic acid cyclopentyl 2-cyanoethyl ester; 1,4-dihydro-2,6-dimethyl-4-(3'nitrophenyl)-pyridine-3,5-dicarboxylic acid allyl 2-cyanoethyl ester; 1,4-dihydro-2,6-dimethyl-4-(3'-nitrophenyl)-pyridine-3,5-dicarboxylic acid 2-methoxyethyl 2-cyanoethyl ester; 1,4-dihydro-2,6-dimethyl-4-(3'-nitrophenyl)-pyridine-3,5-dicarboxylic acid 2-methylthioethyl 2-cyanoethyl ester; 1,4-dihydro-2,6-dimethyl-4-(3'-nitrophenyl)-pyridine-3,5-dicarboxylic acid 2-dimethylaminoethyl 2-cyanoethyl ester; 1,4-dihydro-2,6-dimethyl-4-(3'nitrophenyl)-pyridine-3,5-dicarboxylic acid 2-benzyl-methylamino-ethyl 2-cyanoethyl ester; 1,4-dihydro-2,6-dimethyl-4-(3'-nitrophenyl)-pyridine-3,5-dicarboxylic acid benzyl 2-cyanoethyl ester; 1,4-dihydro-2,6-dimethyl-4-(3'-nitrophenyl)-pyridine-3,5-dicarboxylic acid 3,4-dichlorobenzyl 2-cyanoethyl ester; 1,4-dihydro-2,6-dimethyl-4-(3'-nitrophenyl)-pyridine-3,5-dicarboxylic acid 2,2,2-trifluoroethyl 2-cyanoethyl ester; 1,4-dihydro-2,6-dimethyl-4-(2'-trifluoromethylphenyl)-pyridine-3,5-dicarboxylic acid ethyl 2-cyanoethyl ester; 1,4-dihydro-2,6-dimethyl-4-(3'-cyanophenyl)-pyridine-3,5-dicarboxylic acid isopropyl 2-cyanoethyl ester; 1,4-dihydro-2,6-dimethyl-4-(2'-methoxyphenyl)-pyridine-3,5-dicarboxylic acid methyl 2-cyanoethyl ester; 1,4-dihydro-2,6-dimethyl-4-(3'-chlorophenyl)-pyridine-3,5-dicarboxylic acid isopropyl 2-cyanoethyl ester; 1,4-dihydro-2,6-dimethyl-4-(2'-fluorophenyl)-pyridine-3,5-dicarboxylic acid isopropyl 2-cyanoethyl ester; 1,4-dihydro-2,6-dimethyl-4-(2-pyridyl)-pyridine-3,5-dicarboxylic acid isopropyl 2-cyanoethyl ester; 1,4-dihydro-2,6-dimethyl-4-(3-pyridyl)-pyridine-3,5-dicarboxylic acid isopropyl 2-cyanoethyl ester; 1,4-dihydro-2,6-dimethyl-4-(2-furyl)-pyridine-3,5-dicarboxylic acid isopropyl 2-cyanoethyl ester; 1,4-dihydro-2,6-dimethyl-4-(2-thienyl)-pyridine-3,4-dicarboxylic acid isopropyl 2-cyanoethyl ester; 1,4-dihydro-2,6-dimethyl-4-(4-inolinyl)-pyridine-3,5-dicarboxylic acid isopropyl 2-cyanoethyl ester; 1,4-dihydro-2,6-dimethyl-4-(3'-nitrophenyl)-pyridine-3,5-dicarboxylic acid isopropyl 2chloroethyl ester; 1,4-dihydro-2,6-dimethyl-4-(3'-chlorophenyl)-pyridine-3,5-dicarboxylic acid isopropyl 2-acetoxyethyl ester; 1,4-dihydro-2,6-dimethyl-4-(3'-nitrophenyl)-pyridine-5-dicarboxylic acid isopropyl 2-acetoxyethyl ester; 1,4-dihydro-2,6-dimethyl-4-(2'-trifluoromethylphenyl)-pyridine 3,5-dicarboxylic acid isopropyl 2-benzoyloxyethyl ester; 1,4-dihydro-2,6-dimethyl-4-(3'-nitrophenyl)-pyridine-3,5-dicarboxylic acid isopropyl 2-carbethoxyethyl ester and 1,4-dihydro-2,6-dimethyl-4-(3'-nitrophenyl)-pyridine-3,5-dicarboxylic acid isopropyl 2-benzyloxycarbonyl-ethyl ester.

Suitable hydrolysis agents are, above all, inorganic bases. These preferentially include alkali metal hydroxides, such as sodium hydroxide or potassium hydroxide. Depending on the nature of the organic starting compound, the bases can be employed in molar amounts or in two-fold to three-fold excess.

A large excess of water has proved an advantageous reaction medium. To carry out the reaction under homogeneous conditions, it is as a rule advantageous to add an inert, water-miscible organic solvent. Preferred examples of such solvents are alcohols, such as methanol, ethanol n-propanol or i-propanol; esters, such as dioxane, tetrahydrofurane or 1,2-dimethoxyethane; or pyridine, dimethylformamide, dimethylsulphoxide or hexamethylphosphoric acid triamide.

It has proved particularly advantageous to use aliphatic alcohols (such as alkanols) with 1 to 4 carbon atoms and 1,2-dimethoxyethane as solvents.

The reaction temperatures can be varied within the substantial range of 10° to 100° C., and is preferably between 20° and 50° C. Preferably, it is carried out at room temperature.

The reaction can be carried out under normal pressure but also under elevated pressure. As a rule, normal pressure is used.

In carrying out a preferred embodiment of the process according to the invention, 1 mol of the organic starting compound of the formula (II) is reacted with 1 to 3 mols of an organic base in a suitable aqueous organic solvent mixture. Thereafter, the mixture is diluted with water and extracted with methylene chloride. The aqueous phase is separated off and acidified, whereupon the reaction products according to the invention precipitate. They are filtered off and recrystallised from an inert organic solvent.

The compounds prepared according to the invention have a broad and diverse pharmacological action spectrum. In detail, the following main actions proved demonstrable experimentally:

1. On parenteral, oral and perlingual administration the compounds produce a distinct and long-lasting dilation of the coronary vessels. This action on the coronary vessels is intensified by a simultaneous nitrite-like effect of reducing the load on the heart.

The compounds influence or modify the heart metabolism in the sense of an energy saving.

2. The excitability of the stimulus formation and excitation conduction system within the heart is lowered, so that an anti-fibrillation action demonstrable at therapeutic doses results.

3. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

4. The compounds lower the blood pressure of normotonic and hypertonic animals and can thus be used as anti-hypertensive agents.

5. The compounds have strongly muscular-spasmolytic actions which manifest themselves on the smooth muscle of the stomach, the intestinal tract, the urogenital tract and the respiratory system.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g $C_{14}$-alcohol with $C_{16}$-fatty acid]) or admixture of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example groundnut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 to 250 mg of active ingredient in the case of intravenous administration and 25 to 250 mg of active ingredient in the case or oral administration.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer amounts of from 0.01 mg to 10 mg/kg, especially 0.05 mg to 5 mg/kg, of body weight per day in the case of intravenous administration, and 0.05 mg to 20 mg/kg, especially 0.5 mg to 5 mg/kg, of body weight per day in the case of oral administration, to achieve effective results. Nevertheless, it can at times be necessary to deviate from those dosage rates, and in particular to do so as a function of the nature and body weight of the subject to be treated, and the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

According to the present invention there is further provided novel compounds which are acids of the general formula (I), and their salts, in which, R denotes a 2-nitrophenyl radical, a 3-nitrophenyl radical, a 2-trifluoromethylphenyl radical, a 2-chlorophenyl radical or a 2-methylmercaptopyridyl radical, $R^1$ and $R^2$ denotes methyl groups and X denotes COOH or COOR$^4$, whereby R$^4$ denotes a straight-chain, branched or cyclic alkyl radical with up to 6 carbon atoms, which is optionally interrupted by an oxygen atom in the chain or is substituted by 1 to 2 trifluoromethyl groups or by a

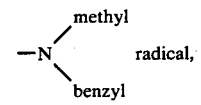

but R$^4$ only denotes a methyl or isobutyl radical when R denotes a 2-nitrophenyl radical.

Of these new compounds those in which R denotes a 2-nitrophenyl radical, and R$^4$ denotes a methyl or an isobutyl radical, may be singled out.

These new compounds are preferentially suitable for use as starting materials for the preparation of dihydropyridine derivatives having a particularly advantageous action, of pure dihydropyridines with different ester groups and of labelled diesters, especially dihydropyridine diesters, which are prepared by customary esterification methods from compounds of the formula (I).

The following Examples illustrate the process of the present invention.

EXAMPLE 1

1,4-Dihydro-2,6-dimethyl-4-(3'-nitrophenyl)-pyridine-3,5-dicarboxylic acid monoisopropyl ester

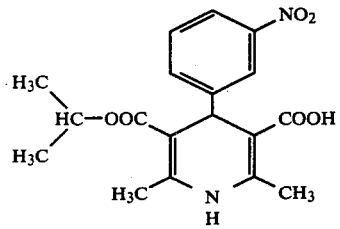

41.3 g (0.1 mol) of 1,4-dihydro-2,6-dimethyl-4-(3'-nitrophenyl)-pyridine-3,5-dicarboxylic acid 5-isopropyl-3-(2-cyanoethyl)ester, in a solution of 12 g (0.3 mol) of sodium hydroxide in 300 ml of water plus 150 ml of 1,2-dimethoxyethane, were stirred for 7 hours at room temperature. The reaction mixture was then diluted with 100 ml of water and repeatedly extracted with methylene chloride. The organic extracts were discarded and the aqueous phase was acidified with dilute hydrochloric acid. Hereupon, the reaction product precipitated. It was filtered off and recrystallised from methanol.

Melting point: 182° to 184° C. (decomposition); yield: 26 g (72%).

The following compounds (Table 1) were obtained analogously to example 1.

TABLE 1

| No. | Formula | Solvent | Melting point | Yield |
|---|---|---|---|---|
| 2 | [structure: 2-NO2-phenyl dihydropyridine with H3C-OOC and COOH, H3C and CH3] | 1,2-dimethoxyethane water | 186° C. (decomposition) | 42% |
| 3 | [structure: 3-NO2-phenyl dihydropyridine with H3COOC and COOH, H3C and CH3] | 1,2-dimethoxyethane water | 203° C. (decomposition) | 81% (crude product) |
| 4 | [structure: 3-NO2-phenyl dihydropyridine with H2C2OOC and COOH, H3C and CH3] | 1,2-dimethoxyethane water | 191° C. (decomposition) | 41% |
| 5 | [structure: 3-NO2-phenyl dihydropyridine with (H5C2)(H3C)HC—OOC and COOH, H3C and CH3] | 1,2-dimethoxyethane water | 153° C. (decomposition) | 60% |
| 6 | [structure: 3-NO2-phenyl dihydropyridine with cyclopentyl-OOC and COOH, H3C and CH3] | 1,2-dimethoxyethane water | 208° C. (decomposition) | 65% |
| 7 | [structure: 3-NO2-phenyl dihydropyridine with H3CO—H2CH2CO2C and COOH, H3C and CH3] | 1,2-dimethoxyethane water | 192° C. (decomposition) | 56% |

TABLE 1-continued

| No. | Formula | Solvent | Melting point | Yield |
|---|---|---|---|---|
| 8 | 4-(3-nitrophenyl)-3-(2-methylthioethoxycarbonyl)-2,6-dimethyl-1,4-dihydropyridine-5-carboxylic acid | 1,2-dimethoxyethane water | 203° C. (decomposition) | 32% |
| 9 | 4-(3-nitrophenyl)-3-(benzyloxycarbonyl)-2,6-dimethyl-1,4-dihydropyridine-5-carboxylic acid | 1,2-dimethoxyethane water | 180° C. (decomposition) | 43% |
| 10 | 4-(2-trifluoromethylphenyl)-3-(ethoxycarbonyl)-2,6-dimethyl-1,4-dihydropyridine-5-carboxylic acid | 1,2-dimethoxyethane water | 151° C. (decomposition) | 37% |
| 11 | 4-(3-nitrophenyl)-3-(phenylsulfonyl)-2,6-dimethyl-1,4-dihydropyridine-5-carboxylic acid | 1,2-dimethoxyethane water | 206° C. (decomposition) | 46% |
| 12 | (+) 4-(3-nitrophenyl)-2,6-dimethyl-1,4-dihydropyridine-3,5-dicarboxylic acid | 1,2-dimethoxyethane water | 194° C. (decomposition) | 60% |
| 13 | 4-(2-pyridyl)-3-(ethoxycarbonyl)-2,6-dimethyl-1,4-dihydropyridine-5-carboxylic acid | 1,2-dimethoxyethane water | 206° C. (decomposition) | 31% |

TABLE 1-continued

| No. | Formula | Solvent | Melting point | Yield |
|---|---|---|---|---|
| 14 | ![structure] pyridin-3-yl 1,4-DHP with H5C2OOC and COOH, 2,6-dimethyl | 1,2-dimethoxyethane water | 205° C. (decomposition) | 32% |
| 15 | ![structure] pyridin-3-yl 1,4-DHP with isopropyl ester (H3C)2HC—OOC and COOH, 2,6-dimethyl | 1,2-dimethoxyethane water | 208° C. (decomposition) | 46% |
| 16 | ![structure] 2-chlorophenyl 1,4-DHP with H3COOC and COOH, 2,6-dimethyl | 1,2-dimethoxyethane water | 205° C. (decomposition) | 78% |

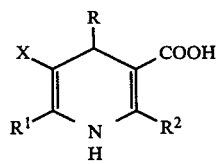

(+)starting material: 3,5-di-(2-cyanoethyl)ester compound

Among the new 1,4-dihydropyridinecarboxylic acid salts of the invention, those salts that are pharmaceutically acceptable are particularly important and are preferred.

The new free 1,4-dihydropyridinecarboxylic acids of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursors' of an active compound of the invention means a compound having a structural formula different from the active compound but which nonetheless, upon administration to an animal or human being is converted in the patient's body to the active compound.

What is claimed is:

1. A process for the production of 1,4-dihydropyridinecarboxylic acid of the formula $$\text{(I)}$$

X—C(R$^1$)=C(R)—C(COOH)=C(R$^2$)—NH— (ring)

or its salt, in which

R is an aryl radical or a heterocyclic radical selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl and quinoxalyl, in which the aryl radical or the heterocyclic radical optionally contains 1 to 3 identical or different substituents selected from phenyl, alkyl, alkenyl, alkinyl, alkoxy, halogen, trifluoromethyl, trifluoromethoxy, alkylamino, nitro, cyano, azido, carboxamido, sulphonamido and $SO_m$—alkyl (in which m is 0, 1 or 2)

$R^1$ and $R^2$ are identical or different and denote a hydrogen atom, a straight-chain or branched alkyl radical, an aryl radical or an aralkyl radical and X (a) is a —COOH group or (b) is a group of the formula —COR$^3$, in which R$^3$ is an optionally substituted alkyl, aryl, aralkyl, amino, monoalkylamino or dialkylamino group, or (c) is a group of the formula —COOR$^4$ in which R$^4$ is a straight-chain, branched or cyclic, saturated or unsaturated hydrocarbon radical which is optionally interrupted by an oxygen or a sulphur atom or by an —SO— or —SO$_2$—group in the chain, and/or which is optionally substituted by one halogen or by 1 or 2 trifluoromethyl groups or by one phenyl, phenoxy, phenylthio or phenylsulphonyl group, which in turn is optionally substituted by halogen, cyano, dialkylamino, alkoxy, alkyl, trifluoromethyl or nitro, or in which the hydrocarbon radical is optionally substituted by pyridyl or amino, these amino groups carrying two identical or different substituents selected from alkyl, alkoxyalkyl, aryl and aralkyl, and these substituents optionally form, with the nitrogen atom, a 5- to 7-membered ring which optionally contains an oxygen or sulphur atom or the N-alkyl grouping as a further hetero-atom, or (d) is a group of the formula —S(O)$_{r}$—R$^5$ in which r$_5$ is 0, 1 or 2 and R$^5$ denotes a straight-chain, branched or cyclic saturated or unsaturated aliphatic hydrocarbon radical, optionally interrupted by an oxygen atom in the chain and/or which is optionally substituted by amino or an aryl radical selected from phenyl, phenoxy, phenylthio, phenylsulphonyl, and pyridinyl, the aryl radicals being optionally substituted by halogen, cyano, dialkylamino, alkoxy, alkyl, trifluoromethyl and nitro, and the amino group being optionally substituted by 2 identical or different substituents selected from alkyl, alkoxyalkyl, aryl or aralkyl, these substituents optionally form, with the nitrogen atom, a 5- to 7-membered ring which optionally contains an oxygen or sulphur atom or the N-alkyl grouping as a further heteroatom, or in which R$^5$ is an aryl radical which optionally contains 1 to 3 identical or different substituents selected from alkyl, alkoxy, halogen, cyano, trifluoromethyl, trifluoromethoxy, dialkylamino and nitro, which comprises hydrolyzing a 1,4-dihydropyridine derivative of the formula

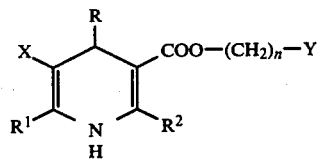

(II)

in which

R, R$^1$, R$^2$ and X have the above-mentioned meaning, n is 1, 2, 3 or 4 and

Y denotes an electron-attracting group under alkaline conditions in the presence of an inert organic solvent in a temperature range from 10° to 100° C.

2. A process according to claim 1 in which R, R$^1$, R$^2$, X, n and Y have the same meanings as in claim 1 with the proviso that the heterocyclic radical of R is substituted by 1 to 3 identical or different substituents selected from those specified in claim 1.

3. A process according to claim 1 for the preparation of a compound of the formula (I) or its salt, in which R is a pyridyl radical or a phenyl radical which contains one or two identical or different substituents selected from halogen, nitro, cyano, trifluoromethyl, azido, trifluoromethoxy or alkoxy with 1 or 2 carbon atoms, R$^1$ and R$^2$ are identical or different and denote a hydrogen atom, an alkyl group with 1 or 2 carbon atoms, a phenyl radical or a benzyl radical and X (a) is the group —COOH or (b) is the group —COR$^3$, in which R$^3$ is an alkyl group with 1 to 4 carbon atoms, or (c) is the group —COOR$^4$, in which R$^4$ is a straight-chain, branched or cyclic, saturated or unsaturated hydrocarbon radical, which is optionally interrupted in the chain by an oxygen or sulphur atom or by the —SO$_2$—group, or denotes a benzyl radical, or (d) is the group —SO$_2$—R$^5$, in which R$^5$ is a straight-chain or branched, saturated or unsaturated hydrocarbon radical with up to 6 carbon atoms, or a phenyl radical.

4. A process according to claim 1, in which the substituent Y in the formula (II) denotes a chlorine atom, a cyano group or an acetoxy group and n is 2.

5. A process according to claim 1, in which the hydrolysis is carried out in the presence of alkali metal hydroxides in a temperature range from 20° to 50° C.

6. A process according to claim 1, in which the solvent is an aliphatic alcohol with 1 to 4 carbon atoms or 1,2-dimethoxyethane.

7. A process according to claims 2 or 3 in which the hydrolysis is carried out in the presence of an alkali metal hydroxide.

8. A process according to any of claims 2 or 3 in which the hydrolysis is carried out in a temperature range from 20° to 50° C.

9. A process according to any of claims 2 or 3 in which the solvent is an aliphatic alcohol with 1 to 4 carbon atoms or 1,2-dimethoxyethane.

10. A process according to claim 1 for the production of a dihydropyridinediester of a compound of formula (I) as defined in claim 1 in which X is a radical (c) which comprises esterifying the free carboxylic acid group of that compound of formula (I) in which X denotes a radical (c).

* * * * *

UNITED STATES PATENT AND TRADEMARK OFFICE
CERTIFICATE OF CORRECTION

PATENT NO. : 4,483,985

DATED : November 20, 1984

INVENTOR(S) : Egbert Wehinger, et al

It is certified that error appears in the above-identified patent and that said Letters Patent is hereby corrected as shown below:

| | |
|---|---|
| 1st Page, under "[22] Filed" | Insert --[30] <u>Foreign Application Priority Data</u>:<br>Germany P 2847237.9 October 31, 1978;<br>Germany P 2921429.7 May 26, 1979-- |
| Col. 1, line 24 | Correct spelling of "hydrolysis" |
| Col. 1, line 26 and Col. 5, line 48 | Delete "m" and substitute --<u>m</u>-- |
| Col. 2, line 29 and Col. 6, line 22 | Delete "r" and substitute --<u>r</u>-- |
| Col. 2, line 64, Col. 5, line 54, Col. 7, line 36, Col. 7, lien 46, Col. 19, lines 42 and 48, Col. 20, line 31 | Delete "n" and substitute --<u>n</u>-- |
| Col. 3, line 12 | After "1" delete "to" and substitute --or-- |
| Col. 3, line 17 | Delete "-axa-" and substitute --oxa-- |
| Col. 8, line 34 | Delete "inolinyl" and substitute --quinolinyl-- |
| Col. 8, line 37 | After "2" insert -- - -- |
| Col. 8, line 40 | After "pyridine-" insert --3,-- |
| Col. 13, Table 1, Formula No. 4 | Delete 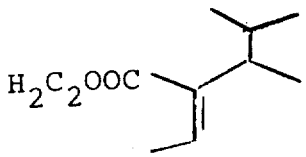 and substitute |

UNITED STATES PATENT AND TRADEMARK OFFICE
CERTIFICATE OF CORRECTION

PATENT NO. : 4,483,985
DATED : November 20, 1984
INVENTOR(S) : Egbert Wehinger, et al It is certified that error appears in the above-identified patent and that said Letters Patent is hereby corrected as shown below:

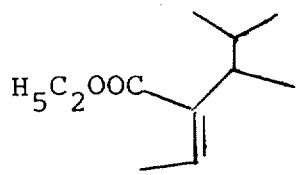

Col. 19, line 7    Delete "$r_5$" and substitute --$\underline{r}$--

Signed and Sealed this

Twenty-third Day of July 1985

[SEAL]

Attest:

DONALD J. QUIGG

Attesting Officer    Acting Commissioner of Patents and Trademarks